United States Patent
Zilla et al.

(10) Patent No.: US 6,702,848 B1
(45) Date of Patent: *Mar. 9, 2004

(54) FOAM-TYPE VASCULAR PROSTHESIS WITH WELL-DEFINED ANCLIO-PERMISSIVE OPEN POROSITY

(76) Inventors: Peter Paul Zilla, 14 Dal Road, Camps Bay (ZA), 8005; Deon Bezuidenhout, 2 Liebenhof, Merriman Avenue, Stellenbosch (ZA), 7600

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/434,649

(22) Filed: Nov. 5, 1999

Related U.S. Application Data

(60) Provisional application No. 60/144,704, filed on Jul. 20, 1999.

(51) Int. Cl.[7] ................................................ A61F 2/06
(52) U.S. Cl. ................................................ 623/1.39
(58) Field of Search ........................ 623/1.39, 1.4, 623/1.23, 1.26; 606/191, 198

(56) References Cited

U.S. PATENT DOCUMENTS

| | | | |
|---|---|---|---|
| 4,286,341 A | * 9/1981 | Greer et al. | 623/1.4 |
| 4,441,215 A | 4/1984 | Kaster | 3/1.4 |
| 4,459,252 A | 7/1984 | MacGregor et al. | 264/46.9 |
| 4,552,707 A | 11/1985 | How | 264/8 |
| 4,605,406 A | 8/1986 | Cahalan et al. | 623/1 |
| 4,657,544 A | 4/1987 | Pinchuk | 623/1 |
| 4,725,273 A | * 2/1988 | Kira | 623/1.39 |
| 4,743,252 A | 5/1988 | Martin, Jr. et al. | 623/1 |
| 4,784,659 A | 11/1988 | Fleckenstein et al. | 623/1 |
| 4,834,746 A | 5/1989 | Kira | 623/1 |
| 4,842,575 A | 6/1989 | Hoffman, Jr. et al. | 600/36 |
| 4,873,308 A | 10/1989 | Coury et al. | 528/75 |
| 4,921,495 A | 5/1990 | Kira | 623/1 |
| 4,932,964 A | 6/1990 | Bittmann et al. | 623/1 |
| 4,941,870 A | 7/1990 | Okada et al. | 600/36 |

(List continued on next page.)

FOREIGN PATENT DOCUMENTS

| | | | |
|---|---|---|---|
| EP | 0 286 220 A1 | 12/1988 | B29C/67/06 |
| EP | 0 315 814 A2 | 5/1989 | C08J/9/26 |
| EP | 0 332 371 A1 | 9/1989 | B29D/23/22 |
| EP | 560279 A1 | 9/1993 | A61L/27/00 |
| EP | 560279 B1 | 9/1993 | A61L/27/00 |
| EP | 0 815 806 A2 | 1/1998 | A61F/2/06 |
| WO | WO 90/06094 | 6/1990 | A61F/2/06 |
| WO | WO 92/09652 | 6/1992 | C08J/9/26 |
| WO | WO 97/15242 | 5/1997 | A61F/2/02 |
| WO | WO 97/47254 | 12/1997 | A61B/19/00 |

OTHER PUBLICATIONS

Annis, et al., An Elastomeric Vascular Prosthesis, *Trans. Am. Soc. Artif. Intern. Organs*, vol. XXIV, 1978, pp. 209–214.

Berkowitz, Henry D, M.D. et al., Pseudointimal Development on Microporous Polyurethane Lattices, *Surgery* Dec. 1972, vol. 72, No. 6, pp. 888–896.

(List continued on next page.)

*Primary Examiner*—Kevin T. Truong
(74) *Attorney, Agent, or Firm*—Kenneth J. Collier; Reed A. Duthler

(57) ABSTRACT

A vascular prosthesis is constructed from a well-defined pore structure to allow uninterrupted ingrowth of connective tissue into a wall of the prosthesis. Several different methods can be used to produce the prosthesis, including a vacuum impregnation technique, a paste molding technique, a paste extrusion technique, a dip coating technique, and a melt extrusion technique. Furthermore, mechanical properties of the prosthesis are matched with mechanical properties of the host vessel, thereby overcoming problems of compliance mismatch.

29 Claims, 3 Drawing Sheets

U.S. PATENT DOCUMENTS

| | | | |
|---|---|---|---|
| 5,024,671 A | 6/1991 | Tu et al. | 623/1 |
| 5,037,377 A | 8/1991 | Alonso | 600/36 |
| 5,108,424 A | 4/1992 | Hoffman, Jr. et al. | 623/1 |
| 5,132,066 A | 7/1992 | Charlesworth et al. | 264/184 |
| 5,197,977 A | 3/1993 | Hoffman, Jr. et al. | 623/1 |
| 5,415,619 A | 5/1995 | Lee et al. | 600/36 |
| 5,549,664 A | 8/1996 | Hirata et al. | 623/1 |
| 5,584,875 A | 12/1996 | Duhamel et al. | 623/1 |
| 5,628,781 A | 5/1997 | Williams et al. | 623/1 |
| 5,709,934 A | 1/1998 | Bell et al. | 428/305.5 |
| 5,770,417 A | 6/1998 | Vacanti et al. | 435/180 |
| 5,807,406 A | 9/1998 | Brauker et al. | 623/11 |
| 6,056,993 A | 5/2000 | Leidner et al. | 427/2.25 |

OTHER PUBLICATIONS

Berkowitz, Henry D, M.D. et al., Pseudointimal Development on Microporous Polyurethane Lattices, *Amer. Soc. Artif. Int. Organs, 1972* vol. XVIII pp. 25–29.

Edwards, Alan et al., Development of a Microporous Compliant Small Bore Vascular Graft, *Journal of Biomaterials Applications* vol. 10—Oct. 1995, pp.171–187.

Hess, F. M.D.et al., Development and Long–Term Fate of a Cellular Lining in Fibrous Polyurethane Vascular Prosthesis Implanted in the Dog Carotid and Femoral Artery, *Journal of Cardiovascular Surgery*, vol. 33, 1992, pp. 358–365.

Hess, F et al. The Endothelialization Process of a Fibrous Polyurethane Microvascular Prosthesis After Implantation in the Abdominal Aorta of the Rat, *Journal of Cardiovascular Surgery*, vol. 24, 1983, pp. 516–524.

Hess, F et al., Seeding of Enzymatically Derived and Subcultivated Canine Endothelial Cells on Fibrous Polyurethane Vascular Prostheses, *Biomaterials*, 1992, vol. 13 No. 10, pp. 657–663.

Hiratzka, Loren F. M.D. et al., In Vivo Comparison of Replamineform, Silastic, and Bioelectric Polyurethane Arterial Grafts, *Arch Surg*, vol. 114, Jun. 1979, pp. 698–702.

Ives, C.L. et al. In Vivo Investigation of a New Elastomeric Vascular Graft (Mitrathane®) *Trans Am Soc Artif Intern Organs 1984*, vol. XXX, pp. 587–590.

Leidner, Jacob et al., A Novel Process for the Manufacturing of Porous Grafts: Process Description and Product Evaluation, *Journal of Biomedical Materials Research*, vol. 17, 229–247.

Lyman, D.J. et al. Development of Small Diameter Vascular Prostheses, *Trans. Am. Soc. Artif. Intern. Organs, 1977*, vol. XXIII, pp. 253–261.

Murabayashi, S. et al. Fabrication and Liong–Term Implantation of Semi–Conmpliant Small Vascular Prosthesis, *Trans Am Soc Artif Intern Organs 1985*, vol. XXXI, pp. 50–55.

Pollock, E. et al., Tissue Ingrowth and Porosity of Biomer, *Trans Am Soc Artif Intern Organs 1981*, vol. XXVII, pp. 405–409.

Uchida, Naoki et al., Compliance Effects on Small Diameter Polyurethane Graft Patency, *Journal of Biomedical Materials Research*, vol. 27, 1269–1279 (1993).

Weber, Jon N. et al. Replamineform: A New Process for Preparing Porous Ceramic, Metal, and Polymer Prosthetic Materials, *Science*, vol. 176, May 26, 1972, pp. 922–924.

White, Rodney A. et al., Preliminary Report: Evaluation of Tissue Ingrowth into Experimental Replamineform Vascular Prostheses, *Surgery*, Feb. 1976, vol. 79, No. 2, pp. 229–232.

Williams, Stuart K. et al. Formation of a Multilayer Cellular Lining on a Polyurethane Vascular Graft Following Endothelial Cell Sodding, *Journal of Biomedical Materials Research*, vol., 26, 103–117.

Wilson, G.J., Anisotropic Polyurethane Nonwoven Conduits: A New Approach to the Design of a Vascular Prostheses, *Trans Am Soc Artif Intern Organs 1983*, vol. XXIX, pp. 260–268.

Annis et al., Trans. Am. Soc. Artif. Intern Organs, vol. XXIV, 1978, pp. 209–214.

Berkowitz, Henry D., et al.,, Amer Soc Artif Int Organs, vol. XVIII, 1972, pp. 25–29.

Berkowitz, Henry D., M.D., et al., Surgery, vol. 72, No. 6, Dec. 1972, pp. 888–896.

Edwards, Alan et al., Jrnl of Biomaterials Applications, vol. 10, Oct. 1995, pp. 171–187.

Hess, F., J. Cardiovasc. Surg., 24, 1983, pp. 516–524.

Hess, F., et al.,, Biomaterials, vol. 13, No. 10, 1992, pp. 657–663.

Hess, F., M.D. et al., Jrnl of Cardio Surg, vol. 22, 1992, pp. 657–663.

Hiratzka, Loren F., M.D., et al., Arch Surg, vol. 114, Jun. 1979, pp. 698–702.

Ives, C.L., et a., Trans Am Soc Artif Intern Organs, vol. XXX, 1984, pp. 587–590.

Leidner, Jacob et al., Jrnl of Biomedical materials Research, vol. 17, pp. 229–247.

Lyman, D.J., et al., Trans Am Soc Artif Intern Organs, vol. XXIII, 1977, pp. 229–247.

Murabayashi, S. et al.,, Trans Am Soc Artif Intern Organs, vol. XXVII, 1985, pp. 50–55.

Pollock, E., et al.,, Trans Am Soc Artif Intern Organs, vol. XXVII, 1981, pp. 405–409.

Uchida, Naoki et al.,, Jrnl of Biomedical Materials Research, vol. 27, 1993, pp. 1269–1279.

Weber, Jon N., et al.,, Science, vol. 176, May 26, 1972, pp. 922–924.

White, R.A., et al., Science, 1972, 176(37): 922–4.

White, Rodney, A., et al.,, Surgery, vol 79, No. 2, Feb. 1976, pp. 229–232.

Williams, Stuart K., et al., Jrnl of Biomedical Materials Research, vol. 26, pp. 103–117.

Wilsin, G.J.,, Trans Am Soc Artif Intern Organs, vol. XXIX, 1983, pp. 260–268.

* cited by examiner

FOAM-TYPE VASCULAR PROSTHESIS WITH WELL-DEFINED ANCLIO-PERMISSIVE OPEN POROSITY

This application claims the benefit of Provisional application Ser. No. 60/144,704, filed Jul. 20, 1999.

FIELD OF THE INVENTION

This invention is directed to a vascular prosthesis having a well-defined pore structure to allow uninterrupted ingrowth of connective tissue into the wall of the prosthesis. Furthermore, mechanical properties of the prosthesis are matched with mechanical properties of a host vessel, thereby overcoming problems of compliance mismatch.

BACKGROUND OF THE INVENTION

Since the early 1950's, when Voorhees observed an essentially thrombus-free silk thread in a prosthesis explanted from a dog, various polymeric materials have been evaluated for use in porous vascular prostheses. Most commercially available synthetic vascular grafts presently in use are made from either expanded polytetrafluoroethylene (e-PTFE), or woven, knitted, or velour design polyethylene terephthalate (PET or Dacron). Dacron grafts are normally used for large vessel replacement (12–22 mm), whereas e-PTFE is generally used for intermediate diameters (6–12 mm). These conventional prosthetic vascular grafts do not permit unrestricted vessel ingrowth from surrounding tissue due mostly to ingrowth spaces that are either too narrow or discontinuous. When used for smaller diameters, these grafts often fail early due to occlusion by thrombosis (fibrous tissue build up) or kinking, or at a later stage because of anastomotic or neointimal hyperplasia (exuberant muscle growth at the interface between artery and graft). Compliance mismatch between the host artery and the synthetic vascular prosthesis, which may result in anastomotic rupture, disturbed flow patterns and increased stresses, is thought to be a causative factor in graft failure. Other causative factors may include the thrombogenicity of the grafts or the hydraulic roughness of the surface, especially in crimped grafts.

In attempts to facilitate ingrowth, the pore size of commercial e-PTFE grafts has been increased. Due to the irregular structure of the pores (between the nodes and internodular fibers), the available ingrowth spaces rapidly narrow down to sub-arteriole dimensions. Various researchers have produced "foam type" grafts, and although compliance matching was achieved to some extent by some, the structures obtained by them have certain disadvantages that prohibit or inhibit the ingrowth of connective tissue. These disadvantages include closed external and/or internal surfaces, closed or semi-closed cell structures with little or no inter-pore communication, and irregularly shaped and sized pores due to irregular filler materials used in the processes.

Because of their unique combination of physical, chemical and biocompatible properties, polyurethanes have been studied and used in medical devices for over thirty years. Enzymatic hydrolysis, auto-oxidation, mineralization, and biologically induced environmental stress cracking of polyester- and polyetherurethanes have led manufacturers of medical polyurethanes to develop more specialized formulations to prevent these occurrences. These new generation polyurethane elastomers are being increasingly accepted as the biomaterials of choice in most applications, especially those requiring compliance. It is not surprising, therefor, that many researchers have used various polyurethane compositions (and other elastomers) to produce vascular grafts. Salt casting, phase inversion, spraying, and replamineform techniques have been used to produce sponge-like structures containing ill-defined pores, while filament winding and electrostatic spinning result in the formation of filamentous or fibrous structures. In the production of many of these devices, researchers have been able to approximate the compliance of natural blood vessels by careful manipulation of the process variables. Nevertheless, the performance of these experimental grafts is generally unsatisfactory. This indicates that compliance matching alone does not result in the desired healing patterns.

There is thus a need or desire in the vascular prosthesis industry for a vascular graft having a well-defined pore structure in its walls to allow uninterrupted ingrowth of connective tissue into the walls of the prosthesis, wherein the problems of compliance mismatch are overcome.

SUMMARY OF THE INVENTION

The present invention is directed to a graft with a porous wall structure containing interconnecting, uniformly shaped pores (i.e. voids) having average diameters between 10 and 300 $\mu$m, more preferably 40–110 $\mu$m. The standard deviation of the diameters of the pores is typically less than 20 $\mu$m, more preferably less than 10 $\mu$m. The openings between the pores are typically in the order of 1100 $\mu$m, more typically 20–50 $\mu$m, depending on the size of the pores. The pores (i.e. voids) in the structure have well-defined, preferably spherical shapes, and the sizes of the ingrowth spaces are readily optimized for uninterrupted tissue and vessel ingrowth. The problem of compliance mismatch encountered with conventional grafts is also addressed by matching mechanical properties of the graft with mechanical properties of a host vessel. These mechanical properties include smoothness, elasticity and structural integrity.

Several different methods can be used to produce the graft of the present invention. In one method, a tube is fashioned from an elastomeric polymer, for example, by molding an admixture of polymer, solvent (for the polymer), and spherical, soluble microbeads of a desired diameter. Extraction of the beads and precipitation of the polymer renders a tubular structure containing well-defined pores (in the tube wall) suitable for use as a synthetic, small-diameter vascular graft prosthesis.

In other methods, a paste comprising a polymer solution, for example, and an extractable filler is prepared and either rolled onto a mandrel, deposited as layers onto a mandrel, or extruded through an annular orifice. The polymer is then precipitated and the filler is extracted.

An alternative method for making the invention involves melt extrusion of a thermoplastic elastomer with blowing agents to create porosity.

With the foregoing in mind, it is a feature and advantage of the invention to provide a synthetic vascular graft that contains interconnecting, well-defined pores.

It is also a feature and advantage of the invention to provide a graft with a porous wall structure containing pores in a very narrow size range.

It is another feature and advantage of the invention to provide a graft with well-defined pores wherein the sizes of the ingrowth spaces are readily optimized for uninterrupted tissue and vessel ingrowth into the wall of the prosthesis.

It is yet another feature and advantage of the invention to provide a graft wherein mechanical properties of the graft are matched with mechanical properties of the host vessel, thereby overcoming problems of compliance mismatch.

It is a further feature and advantage of the invention to provide a method for producing a graft with interconnecting, well-defined pores.

DEFINITIONS

Figure 1:
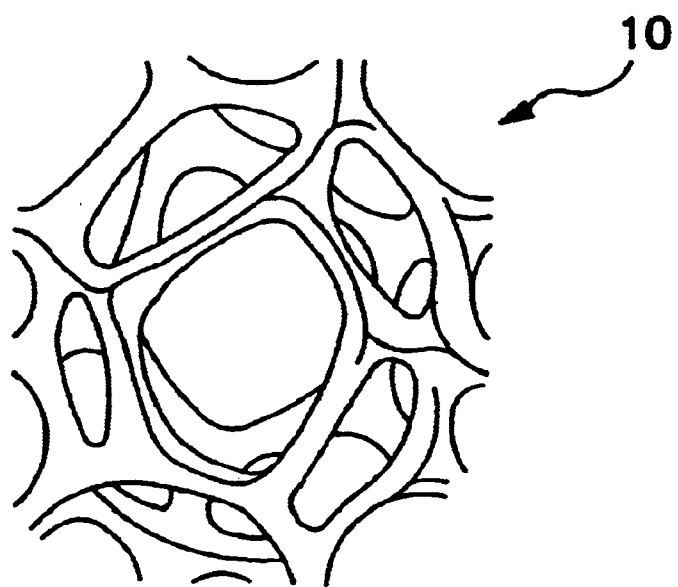
FIG. 1 is a perspective view of a unit cell structure of the invention.

The term "extractable filler" means any polymeric or other filler material that is soluble and/or extractable by a solvent other than the solvent used for the graft material. The material is preferably spherical in shape with average diameters ranging in size from 10 to 300 micrometers, more preferably from 40 to 110 micrometers. The beads are fractionated according to size, for example by sieving so that the individual fractions have a narrow size distribution. One example would be beads with a diameter of 85±10 $\mu$m, where 85 indicates the average size and 10 $\mu$m indicates the standard deviation. Examples of suitable materials include protein beads, e.g. alginate, gelatin, carbohydrates (sugar, dextrose, etc.), inorganic and organic salts. Water soluble fillers are suitable when water is the precipitation solvent and the filler extractor.

The term "filler extraction solvent" means any solvent capable of dissolving the extractable filler without adversely affecting the graft structure. For example, water is a suitable filler extraction solvent for water soluble fillers.

The term "precipitation solvent" means any solvent that is capable of precipitating the graft material from solution. The precipitation solvent and the graft material solvent are usually miscible in all proportions. Examples of suitable precipitation solvents include: water, ethanol, acetone, or combinations of any of these. The filler extraction solvent and the precipitation solvent may or may not be the same solvent.

The term "graft material" means any polymeric or other material that can be dissolved in a suitable solvent and re-solidified after graft manufacture by air-drying, phase inversion, or combinations thereof. Examples of suitable graft materials include: thermoplastic elastomers including thermoplastic polyurethanes, e.g. Pellethane, Biomer type polyurethanes, Chronoflex, Hydrothane, Estane, Elast-Eon, Texin, Biomer, Surethane, Corethane, Carbothane, Techoflex, Tecothane and Biospan. In particular, a polyurethane developed by Medtronic and described in U.S. Pat. No. 4,873,308 is an example of a suitable graft material.

The term "graft material solvent" means any solvent capable of dissolving the graft material. Examples of suitable solvents for polyurethanes include: N-methyl pyrrolidone (NMP), N,N dimethyl diacetamide (DMAC), 1,4 dioxane, etc.

The term "graft material solution" means a solution of the graft material in the graft material solvent in concentrations ranging from 1 to 40% by mass, more typically 5 to 30% by mass, usually 10 to 25% by mass.

The term "graft material paste" means an admixture consisting of a graft material solution and an extractable filler. The ratio of filler to graft material in the solution can range from 20:1 to 1:1, more typically from 10:1 to 5:1 (ratios by mass).

The term "chemical blowing agent" means any material that decomposes to form a gas, e.g. $CO_2$ or $N_2$, wherein the gas creates pores in the graft material. Examples of chemical blowing agents include bicarbonates, N-nitroso compounds, azides, azodicarbonamides, and a variety of other agents.

The term "physical blowing agent" means either a liquid or a gas that is introduced to molten graft material under pressure, wherein evaporation of the liquid or expansion of the gas creates bubbles that form pores in the graft material. Examples of physical blowing agents include: chloro-fluoro carbons (e.g. freon), pentane, and hexane.

DETAILED DESCRIPTION OF THE PRESENTLY PREFERRED EMBODIMENTS

An improved prosthetic vascular graft can be created with a synthetic scaffold of transmural ingrowth channels which are characterized by a continuous, uninterrupted, well-defined dimension. A simulated cell structure with unit cells approximating pentagonal dodecahedrons allows such channels to be formed. A unit cell created in a foam type structure can be, and often is, represented by an idealized pentagonal dodecahedron. A process for producing such well-defined pores (i.e. voids) in a synthetic scaffold can be achieved using spherical, soluble microbeads as an extractable filler. The process is explained in detail below.

Figure 2:
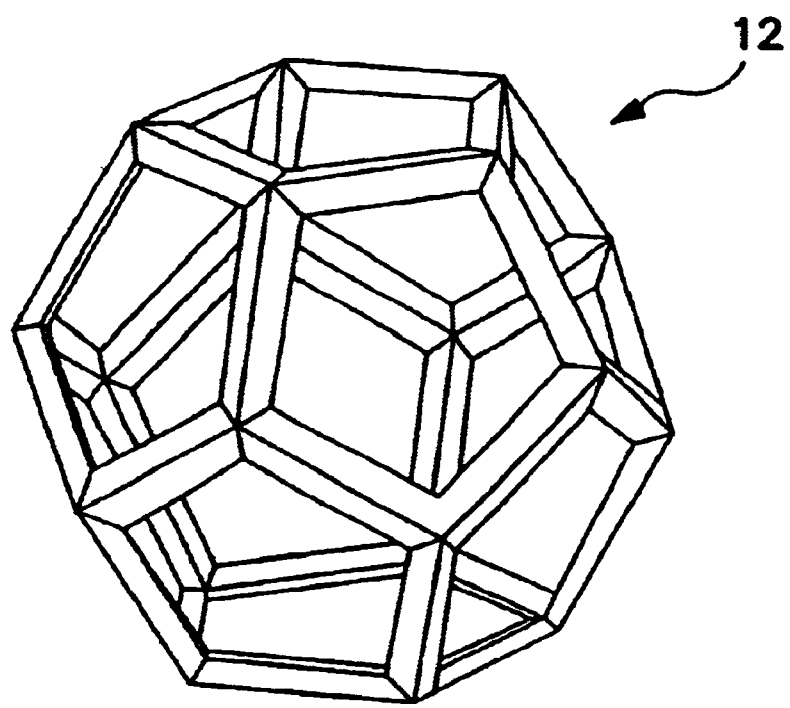
FIG. 2 is a perspective view of a pentagonal dodecahedron.

FIG. 1 shows a typical unit cell 10 created in a foam type structure. FIG. 2 shows a pentagonal dodecahedron 12. A simulated unit cell 10 achieved in the present invention resembles the pentagonal dodecahedron 12, but may vary in the number of sides or the simulated unit cell 10 may be somewhat oblong. A structure containing such multi-sided unit cells in a very narrow size range is well-defined, and sizes of ingrowth channels are readily calculated.

Figure 4:
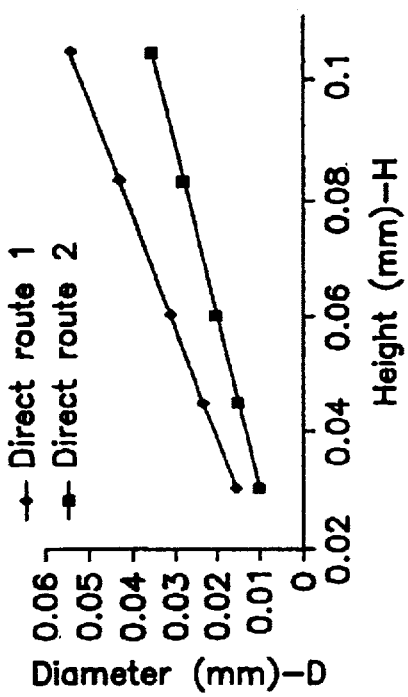
FIG. 4 is a graphical representation of continuous ingrowth diameter as a function of height of the dodecahedron of FIG. 3.
Figure 3:
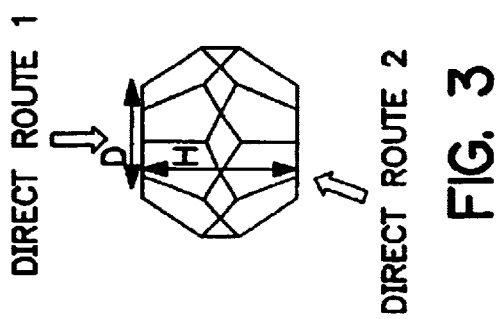
FIG. 3 is a cross-sectional view of a pentagonal dodecahedron.

FIG. 3 shows two different possible direct routes which may be used as ingrowth channels in a pentagonal dodecahedron. Direct Route 1 enters the cell at an angle perpendicular to a face of the cell. Direct Route 2 enters the cell at an angle non-perpendicular to a face of the cell. FIG. 4 is a graphical representation of a correlation between a continuous ingrowth diameter (D) of each of the two routes in FIG. 3 as a function of the dodecahedron's height (H) in FIG. 3. As can be seen in FIG. 4, as the height of the dodecahedron increases, the continuous ingrowth diameter increases more rapidly for routes entering the cell at an angle perpendicular to a face of the cell than for routes entering the cell at an angle non-perpendicular to a face of the cell. Whether the angle of entry is perpendicular or not, the cells provide ample ingrowth channels of continuous, uninterrupted, well-defined dimensions.

Figure 5:
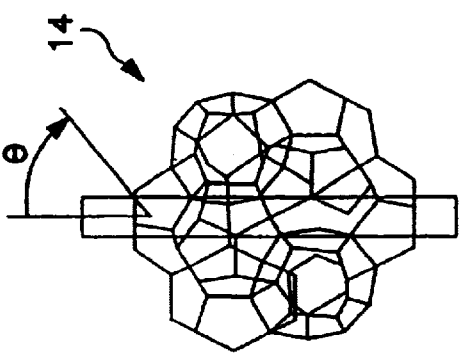
FIG. 5 is a cross-sectional view of a cluster of pentagonal dodecahedrons.

FIG. 5 shows a structure 14 including a cluster of pentagonal dodecahedrons with a possible route indicated, along with an illustrated plane angle ($\theta$) measured against a line running through the cluster of dodecahedrons perpendicular to the face of the dodecahedron at which it enters.

Figure 6:
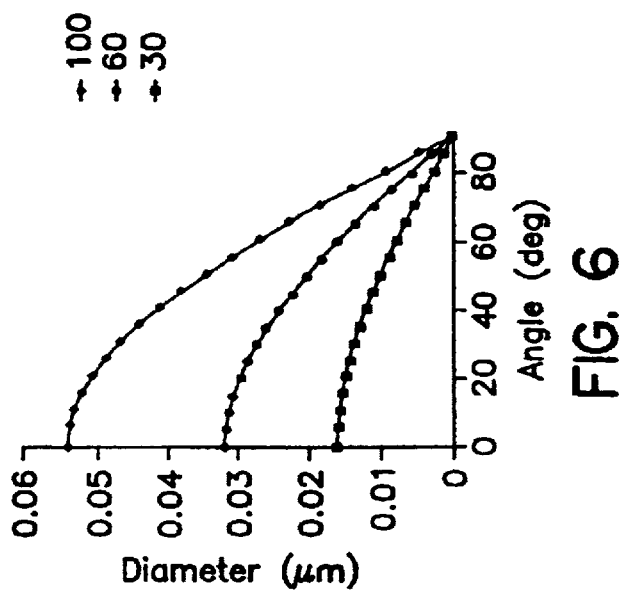
FIG. 6 is a graphical representation of continuous ingrowth diameter as a function of a plane angle through the dodecahedron in FIG. 5.

FIG. 6 is a graphical representation of a diameter of a path through the well-defined dodecahedron structure as the plane angle is altered for various bead sizes: 30, 60 and 100 microns. As can be seen in FIG. 6, when the plane angle is 0°, the diameter of a continuous pore is slightly larger than half the diameter of the bead. Thus, there is quite a large area in which continuous ingrowth of connective tissue can occur. Although not accounted for in FIG. 6, but of great importance, is the fact that if the ingrowing tissue encounters a narrowing of the direct path due to high angles of incidence, a "new", more direct route, can easily be found after a small angle change. Thus, the well-defined porosity is oriented in such a way as to allow for circumferential and longitudinal orientation from radial ingrowth.

In addition to providing well-defined pores, in order to promote ingrowth of connective tissue, it is important that mechanical properties of the graft (especially smoothness, elasticity and structural integrity) are matched with mechanical properties of the host vessel, thereby overcoming problems of compliance mismatch. Although the structure of blood vessels varies through the body, a "typical" artery includes three distinct layers, each performing specific basic functions. An intima, which includes an endothelium attached to a basement membrane, provides a non-thrombogenic blood contacting surface. A media contains smooth muscle cells (SMC's) as well as elastic and other intercellular connective and matrix materials, and supplies two other important properties to the blood vessel, namely compliance and contractility. In order to achieve these properties, the tissues are oriented in a helical fashion in this medial layer. Another important property, namely structural integrity, is provided by an adventitia. The configuration of collagen fibers in this layer provides for "stiffening" of the vessel when subjected to high internal pressures, i.e. a decrease in compliance with increased strain.

In designing the vascular prosthesis of the invention to result in formation of a neo-artery mimicking the properties of a natural vessel, material for the scaffold should have biostability, processability, availability, and desirable mechanical properties. The porous scaffold should provide high porosity for maximal cell ingrowth and minimal bulk compressibility (to allow for compressibility associated with contractility). The prosthesis should have structural integrity and viscoelastic properties similar to those observed for natural vessels. Furthermore, in order to minimize foreign body reaction and to encourage differential cell ingrowth, the scaffold should also exhibit long-term in-vivo stability. Examples of suitable scaffold materials include thermoplastic elastomers, particularly thermoplastic polyurethanes. The well-defined porosity should be oriented in such a way as to allow for circumferential and longitudinal orientation from radial ingrowth to allow physiological contractility. Such orientation is provided by the pentagonal dodecahedron, as illustrated in FIGS. 3–6. Furthermore, the prosthesis must have structural integrity and viscoelastic properties similar to those observed for natural vessels.

Selection of a suitable filler material to create the pores requires careful consideration. When choosing an extractable filler material, the material should be: non-soluble in the solvent used to dissolve the scaffold material; readily soluble in the precipitation solution or other non-solvent for the scaffold material; crush resistant to withstand mixing and forming of pastes; and non-toxic.

Fractionated salt crystals ($NaHCO_3$, and others) are a ready source of extractable fillers. However, their aspect ratios and fairly wide size distributions (even after careful sieving) make them less than ideal candidates for use in the production of foamed structures. Spherical, soluble microbeads can be manufactured to narrow tolerances. The use of these spherical beads contributes to the production of porous "foam" scaffolds that are much better defined than those obtainable from salt crystals.

The extractable filler comprises uniformly shaped particles, preferably spherical in shape. The average diameters of the particles, as well as the resulting pores, range in size from 10 to 300 micrometers, more preferably from 40 to 110 micrometers. The standard deviation of the particle diameters and corresponding pore sizes are preferably within a controlled range of 20 $\mu$m of one another, more preferably within 10 $\mu$m of one another. In an embodiment wherein the particles and pores are not spherical but are uniformly shaped, the particles and pores can still be maintained in a controlled range of volume. For example, spherical particles and pores having diameters maintained in a controlled range where the standard deviation is less than 20 $\mu$m will correspondingly have volumes maintained in a controlled range where the standard deviation will be less than $4.2 \times 10^{-6}$ mm$^3$ (volume of a sphere=$\frac{4}{3}\pi(radius)^3$). Similarly, non-spherical particles and pores that are uniformly shaped can have volumes maintained in a controlled range where the standard deviation will be less than $4.2 \times 10^{-6}$ mm$^3$.

Figure 7:
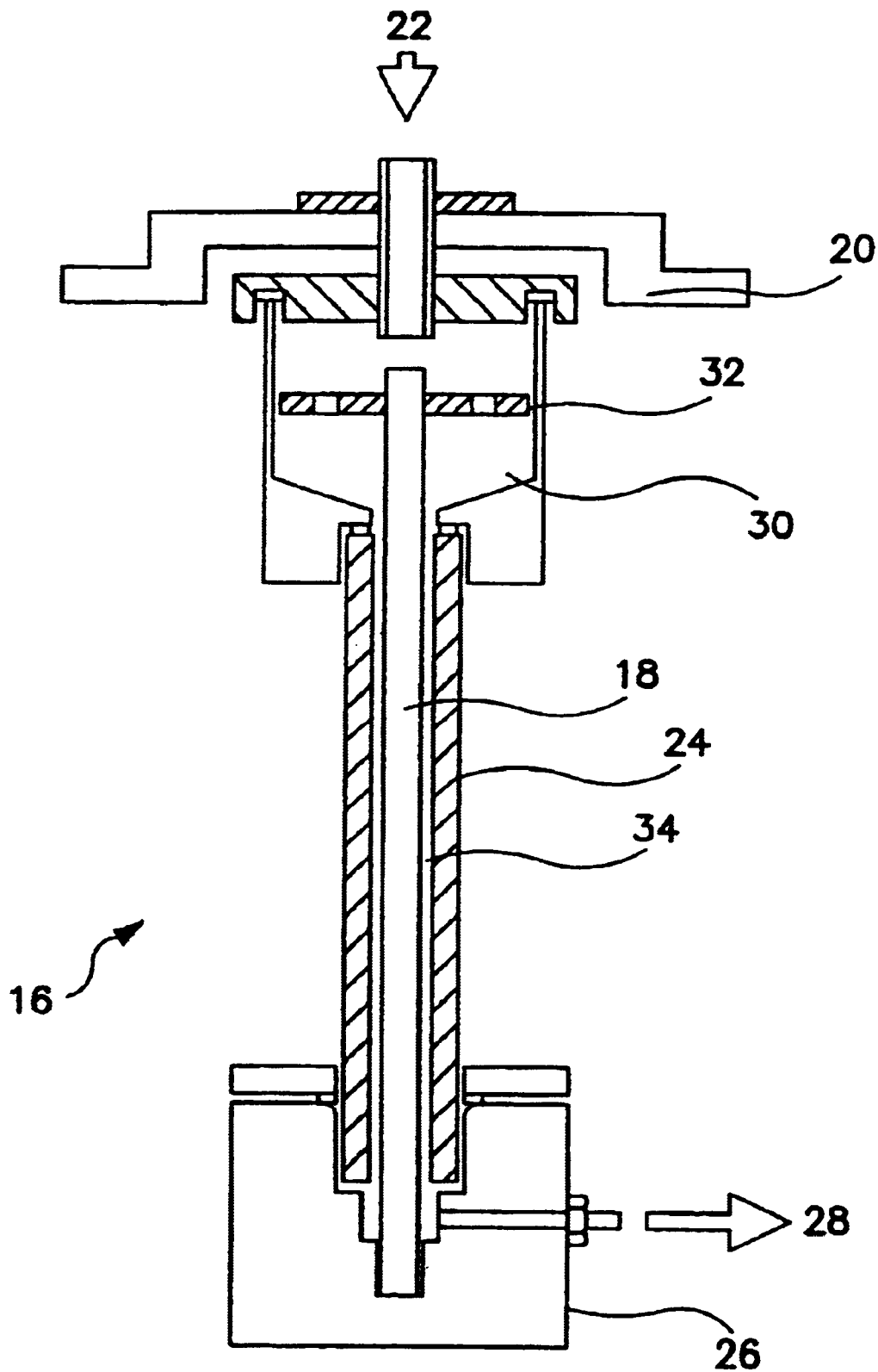
FIG. 7 is a schematic view of a casting device used in producing the vascular prosthesis of the invention.

Several different methods can be used to produce the vascular grafts of the present invention. The most preferred method for producing the grafts of the present invention is a vacuum impregnation technique. Referring to FIG. 7, this method involves assembling a mandrel 18 in a custom-designed casting device 16. The casting device includes a top manifold 20 that allows for application of air pressure 22 to a top portion of a mold or molds 24. A bottom manifold 26 of the device allows for application of a vacuum 28 to a bottom portion of the mold or molds 24. Any number of the molds 24 is clamped between the top and bottom manifolds 20 and 26. Although any number of molds 24 can be used, a manageable number of molds is in the range of 1–20 molds, while a preferred number of molds is in the range of 6–10 molds.

The molds 24 are cylindrical tubes made of glass or other suitable materials with an inside diameter corresponding to a desired outside diameter of a resulting graft. The molds 24 are used in conjunction with cylindrical central rods 18. The cylindrical central rods 18 are made of stainless steel, glass or other suitable materials with an outside diameter corresponding to a desired inner diameter of a resulting graft. Also used in conjunction with the molds 24 is a reservoir 30 for graft material solution and a centralizing spacer 32.

Once the casting device 16 is assembled, the grafts are formed by filling an annular space 34 between the central rod 18 and the tube 24 with an extractable filler. Suitable filler materials include alginate, gelatin, carbohydrates, inorganic and organic salts. The reservoir 30 is filled with a graft material solution comprising graft material in a graft material solvent. Suitable graft materials include thermoplastic elastomers including thermoplastic polyurethanes, such as Pellethane, Biomer type polyurethanes, Chronoflex and Hydrothane. In particular, a polyurethane developed by Medtronic and described in U.S. Pat. No. 4,873,308 is an example of a suitable graft material. Suitable graft material solvents include N-methyl pyrrolidone (NMP), N,N dimethyl diacetamide (DMAC), 1,4 dioxane, etc. Concentration of the graft material in the graft material solvent ranges from 1 to 40% by mass, more typically 5 to 30% by mass, usually 10 to 25% by mass. The concentration depends on various factors, including composition of the graft material, composition of the graft material solvent, and viscosity of the solution. The top manifold 20 is then closed and pressure 22 is applied to the top manifold 20 and/or vacuum 28 is applied to the bottom manifold 26 to force the graft material solution into interstices between the packed extractable filler. The amount of pressure should be on the order of about atmospheric to 15 bar, more preferably 5 to 8 bar. The amount of vacuum should be on the order of about atmospheric to −1 bar, more typically about −0.9 bar.

After the graft material solution is forced into the interstices, the tube 24, graft and rod 18 are removed from the device 16. Precipitation of the graft (defined as removal of the graft material solvent) is begun with immersion into precipitation solvent. Suitable precipitation solvents include water, ethanol, acetone, or combinations of any of these. The central rod 18 is then removed from the graft and the tube 24. Precipitation of the graft material and extraction of the graft material solvent are completed by extended immersion in the precipitation solvent. The precipitated graft is removed from the tube 24. The extractable filler is extracted from the precipitated graft material to produce the porous structure of the invention. The filler can be extracted using a filler extraction solvent, such as water. The precipitation and extraction may be effected either simultaneously or consecutively.

Another method for producing the porous structure of the invention is a paste molding technique. In this method, a paste is prepared from an extractable filler and a graft material solution including graft material and graft material solvent, as described above. The paste contains the filler and the graft material in a ratio of mass between 20:1 and 1:1, respectively. More typically the ratio is between 10:1 and 5:1. A desired thickness of paste is rolled onto a mandrel, wherein the mandrel has an outer diameter equal to a desired internal diameter of a resulting graft. The internal diameter of the graft is preferably between 1 mm and 20 mm, more preferably in the range of 2 to 6 mm for small diameter vessel replacement. The thickness of the paste can vary from 0.1 to 5 mm, more preferably from 0.4 to 1.5 mm, depending on the diameter of the graft. The graft material solution is then precipitated by immersion in precipitation solvent, and the filler is extracted by immersion in a filler extraction solvent, as described above. The precipitation and extraction may be effected either simultaneously or consecutively.

Yet another method for producing the porous structure of the invention is a paste extrusion technique. In this method, a paste is prepared from an extractable filler and a graft material solution comprising graft material and graft material solvent, as described above. The paste is extruded through an annular orifice. The graft material solution is then precipitated by immersion in precipitation solvent, and the filler is extracted by immersion in filler extraction solvent. The precipitation and extraction may be effected either simultaneously or consecutively.

A further method for producing the porous structure of the invention is a dip coating technique. In this method, a paste is prepared (as described above) from an extractable filler and a graft material solution including graft material and graft material solvent. The paste is deposited in consecutive layers onto a mandrel. The graft material solution is then precipitated by immersion in precipitation solvent, and the filler is extracted by immersion in filler extraction solvent. The precipitation and extraction may be effected either simultaneously or consecutively.

Another method for producing the porous structure of the invention is a melt extrusion technique. In this method, a thermoplastic elastomer is extruded with the use of physical and/or chemical blowing agents to produce a foamed graft. Suitable thermoplastic elastomers include thermoplastic polyurethanes, such as Pellethane, Biomer type polyurethanes, Chronoflex, and Hydrothane. Suitable chemical blowing agents include sodium bicarbonate and azodicarbonamides. Suitable physical blowing agents include chloro-fluoro carbons (e.g. freon), pentane, and hexane. The foamed graft is then annealed and reticulated, where needed, to effect an open-cell structure.

There are various types of post-treatment for converting closed cell foams to open cell foams, which essentially entails removing a thin membrane between the cells or pores. One method involves heat treatment. By treating the closed cell foam in a controlled, elevated temperature environment, it is possible to melt the thin membrane without melting the rest of the material. The temperature depends on the graft material. Another method for converting closed cell foams to open cell foams is a mechanical method. By crushing the closed cell foam between rollers or a similar device, the thin membrane will rupture due to the pressure in the pore. A third method is another mechanical method wherein explosive gasses (e.g. stoichiometric ratios of $O_2/H_2$) are infiltrated into the pores. The cells are ruptured by ignition of these gasses. Yet another method is a chemical method whereby the foam is subjected to hydrolysis, thereby destroying the thinner membranes more rapidly than the thicker ribs defining the pores. Any of these methods can be used alone or in combination to produce open cell foams.

A final method of producing the graft involved the use of a process whereby the foamed tube is formed by the reaction of monomeric substances (e.g. diisocyanates and diols when polyurethanes are required) with suitable blowing agents (e.g. water). As those skilled in the art will know, the reaction of these reagents with one another in an enclosed cylindrical space (reaction injection molding or RIM process) or in a modified extruder assembly would yield the desired porous graft. Reticulation, removal of possible interior and/or exterior skin, and other post production techniques may be employed to produce the open-cell porosities needed for the ingrowth of living tissue.

Static burst tests show that the grafts should easily be able to withstand pressures associated with iliac implantation. However, high porosity scaffolds often lack structural integrity to withstand physiological pressures and stresses caused by sutures at the anastomoses. Reinforcing fibers can be incorporated into the graft design in any of the described methods to alleviate this problem. The reinforcing fibers can be incorporated into the grafts by winding the fibers around the scaffold while the graft material is in a paste or solution form, for example. Suitable fibers include either elastic or non-elastic non-degradable material, or a combination of elastic and non-elastic materials. Additionally, a reinforcing material that is either elastic or non-elastic, and is degradable in vivo, can be used in combination with the non-degradable material to provide initial strength to the graft. The reinforcement material that is degradable in vivo degrades as the graft is populated by ingrowing cells and accompanying extracellular matrix material. Ingrowing material tends to stiffen the graft; therefore, a degradable fiber can be used to give initial strength to the graft without making the graft overly stiff after ingrowth. The non-extractable fiber typically has a diameter ranging in size from 10 to 100 micrometers. Examples of suitable non-elastic, non-degradable materials include polyethylene terephthalate (PET, Dacron) and polytetrafluoroethylene (PTFE). Examples of suitable elastic nondegradable materials include thermoplastic polyurethanes, e.g. M48, Pellethane (or clones), Biomer (or clones), or any other biocompatible elastomer. Degradable polyurethanes can serve as degradable reinforcing fibers.

The above-described methods can also be used to produce other items, such as, for example, a biosynthetic heart valve, a sewing ring, or a stent.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A vascular graft prosthesis comprising:
   a polymeric tubular structure having a wall;
   wherein the wall is formed by 3-dimensional unit cells and
   the three dimensional unit cells have interconnecting, uniformly shaped pores.

2. The vascular graft prosthesis of claim 1 wherein the tubular structure has an internal diameter in a range of 1–20 mm.

3. The vascular graft prosthesis of claim 1 wherein the tubular structure has an internal diameter in a range of 2–6 mm.

4. The vascular graft prosthesis of claim 1 wherein the average diameters of the pores are in a range of 10–300 $\mu$m.

5. The vascular graft prosthesis of claim 1 wherein the average diameters of the pores are in a range of 40–110 $\mu$m.

6. The vascular graft prosthesis of claim 1 wherein the polymeric tubular structure comprises an elastomer.

7. The vascular graft prosthesis of claim 1 wherein the elastomeric polymeric tubular structure comprises a polyurethane.

8. The vascular graft prosthesis of claim 1 wherein the elastomeric polymeric tubular structure comprises a segmented aliphatic polyurethane.

9. The vascular graft prosthesis of claim 1 wherein the elastomeric polymeric tubular structure comprises a material selected from the group consisting of Pellethane, Chronoflex, Hydrothane, Estane, Elast-Eon, Texin, Biomer, Surethane, Corethane, Carbothane, Techoflex, Tecothane and Biospan.

10. The vascular graft prosthesis of claim 1 wherein the pores are spherically shaped.

11. The vascular graft prosthesis of claim 1 further comprising reinforcing fibers in the elastomeric polymeric tubular structure.

12. The vascular graft prosthesis of claim 11 wherein the reinforcing fibers comprise a non-elastic, non-degradable material.

13. The vascular graft prosthesis of claim 11 wherein the reinforcing fibers comprise an elastic, non-degradable material.

14. The reinforcing fibers of claim 12 further comprising an elastic, non-degradable material.

15. The reinforcing fibers of claim 12 further comprising a material degradable in vivo.

16. The reinforcing fibers of claim 13 further comprising a material degradable in vivo.

17. The reinforcing fibers of claim 14 further comprising a material degradable in vivo.

18. The vascular graft prosthesis of claim 11 wherein the reinforcing fibers have diameters in a range of 10 to 100 micrometers.

19. The vascular graft prosthesis of claim 1 wherein at least 85% of the pores have diameters within 20 $\mu$m of one another.

20. The vascular graft prosthesis of claim 1 wherein at least 95% of the pores have diameters within 20 $\mu$m of one another.

21. The vascular graft prosthesis of claim 1 wherein substantially all of the pores have diameters within 20 $\mu$m of one another.

22. The vascular graft prosthesis of claim 1 wherein the pores have multiple sides.

23. A vascular graft prosthesis comprising:
    an elastomeric polymeric tubular structure having a wall; and
    interconnecting, uniformly shaped pores formed by the tube walls;
    wherein at least 75% of the pores have volumes within $4.2 \times 10^{-6}$ mm$^3$ of one another.

24. The vascular graft prosthesis of claim 23 wherein at least 85% of the pores have volumes within $4.2 \times 10^{-6}$ mm$^3$ of one another.

25. The vascular graft prosthesis of claim 23 wherein at least 95% of the pores have volumes within $4.2 \times 10^{-6}$ mm$^3$ of one another.

26. The vascular graft prosthesis of claim 23 wherein substantially all of the pores have volumes within $4.2 \times 10^{-6}$ mm$^3$ of one another.

27. A prosthetic heart valve comprising:
    an elastomeric polymeric tubular structure having a wall; and
    interconnecting, uniformly shaped pores in the tube wall;
    wherein at least 75% of the pores have diameters within 20 $\mu$m of one another.

28. A sewing ring comprising:
    an elastomeric polymeric tubular structure having a wall; and
    interconnecting, uniformly shaped pores in the tube wall;
    wherein at least 75% of the pores have diameters within 20 $\mu$m of one another.

29. A stent comprising:
    an elastomeric polymeric tubular structure having a wall; and
    interconnecting, uniformly shaped pores in the tube wall;
    wherein at least 75% of the pores have diameters within 20 $\mu$m of one another.

* * * * *

UNITED STATES PATENT AND TRADEMARK OFFICE
CERTIFICATE OF CORRECTION

PATENT NO. : 6,702,848 B1  Page 1 of 1
APPLICATION NO. : 09/434649
DATED : March 9, 2004
INVENTOR(S) : Peter Paul Zilla and Deon Bezuidenhout It is certified that error appears in the above-identified patent and that said Letters Patent is hereby corrected as shown below:

On the title page, item 54 + column 1, line 2;
Title: "…...Defined Anclio….." should read      --…..Defined Angio…....--

Signed and Sealed this

Twenty-fifth Day of December, 2007

JON W. DUDAS
*Director of the United States Patent and Trademark Office*